(12) United States Patent
Fujitani et al.

(10) Patent No.: US 12,266,435 B2
(45) Date of Patent: Apr. 1, 2025

(54) MEDICINE DISPENSING APPARATUS

(71) Applicant: TAKAZONO CORPORATION, Osaka (JP)

(72) Inventors: Noboru Fujitani, Kadoma (JP); Masayuki Hironaga, Hirakata (JP)

(73) Assignee: TAKAZONO CORPORATION, Kadoma (JP)

( * ) Notice: Subject to any disclaimer, the term of this patent is extended or adjusted under 35 U.S.C. 154(b) by 378 days.

(21) Appl. No.: 17/913,661

(22) PCT Filed: Mar. 4, 2021

(86) PCT No.: PCT/JP2021/008334
§ 371 (c)(1),
(2) Date: Sep. 22, 2022

(87) PCT Pub. No.: WO2021/192880
PCT Pub. Date: Sep. 30, 2021

(65) Prior Publication Data
US 2023/0116594 A1 Apr. 13, 2023

(30) Foreign Application Priority Data

Mar. 24, 2020 (JP) .................................. 2020-052904

(51) Int. Cl.
*G16H 20/13* (2018.01)
*A61J 7/00* (2006.01)
(52) U.S. Cl.
CPC ............ *G16H 20/13* (2018.01); *A61J 7/0084* (2013.01)
(58) Field of Classification Search
CPC .... G16H 20/13; G07F 17/0092; B65G 1/1378
See application file for complete search history.

(56) References Cited

U.S. PATENT DOCUMENTS 11,954,962 B2 * 4/2024 Tanaka .................... G07F 9/026
2010/0030667 A1 2/2010 Chudy et al.
(Continued)

FOREIGN PATENT DOCUMENTS

| JP | H07-33214 A | 2/1995 |
| JP | H10-201824 A | 8/1998 |

(Continued)

OTHER PUBLICATIONS

Office Action dated Feb. 13, 2024, issued in counterpart JP Application No. 2023-121547, with English translation. (5 pages).

(Continued)

*Primary Examiner* — Timothy R Waggoner
(74) *Attorney, Agent, or Firm* — WHDA, LLP

(57) ABSTRACT

A conveyer conveys a medicine container, from a storage site storing a plurality of the medicine containers each containing a medicine, to a delivery site where the medicine is removed from the medicine container, and returns, from the delivery site to the storage site, the medicine container from which the contained medicine is partially removed. A standby site where the medicine container unloaded from the storage site and directed toward the delivery site is allowed to stand by is located between the storage site and the delivery site. The medicine container containing the medicine determined not to be used for subsequent medicine preparation is returned from the standby site to the storage site. The medicine container containing the medicine determined to be used also for the subsequent medicine preparation is caused to stand by at the standby site until the subsequent medicine preparation, without being returned to the storage site.

12 Claims, 7 Drawing Sheets

(56) References Cited

U.S. PATENT DOCUMENTS

2013/0092702 A1\* 4/2013 Holmes ................... G07F 11/60
  221/191
2013/0168405 A1\* 7/2013 Yuyama .................. G07F 11/42
  221/277

FOREIGN PATENT DOCUMENTS

| JP | 2000-118635 A | 4/2000 |
| JP | 2007-215575 A | 8/2007 |
| JP | 2015-223460 A | 12/2015 |
| WO | 2016/047487 A1 | 3/2016 |

OTHER PUBLICATIONS

International search Report dated Apr. 20, 2021, issued in counterpart Application No. PCT/JP2021/008334. (2 pages).

\* cited by examiner

FIG.8
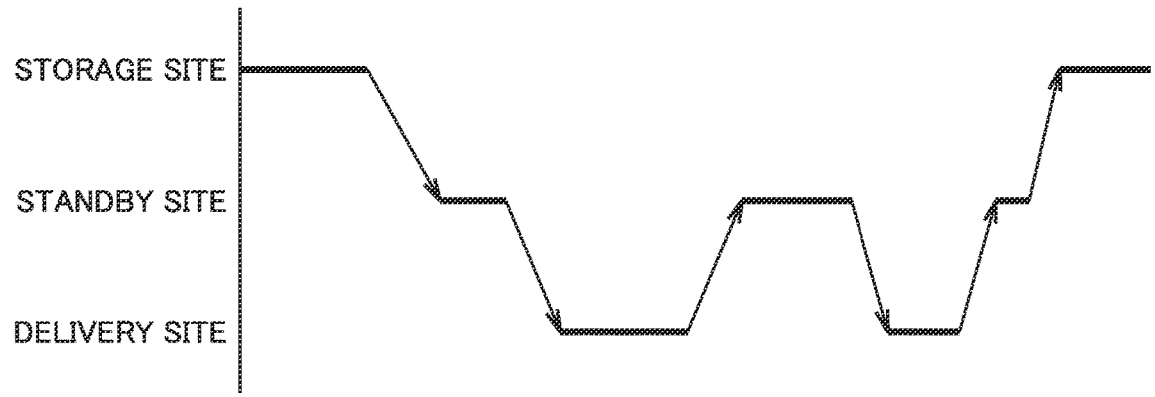
FIG.9
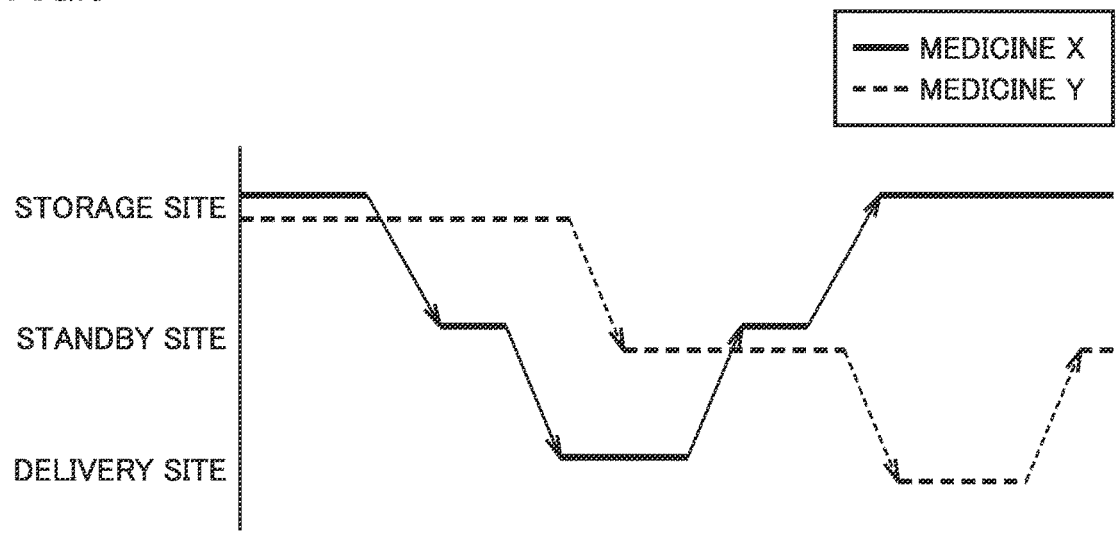
FIG.10
| PRESCRIPTION DATA | | 1 | 2 | 3 | 4 | 5 | 6 | 7 | 8 | 9 | 10 |
|---|---|---|---|---|---|---|---|---|---|---|---|
| MEDICINE | A | 1 | 1 | | 1 | 1 | 1 | 1 | 1 | | 1 |
| | B | 1 | | 1 | 1 | 1 | | | 1 | | 1 |
| | C | | 1 | | 1 | | | 1 | | 1 | |
| | D | | 1 | | | 1 | 1 | | | | |
| | E | | | 1 | | | | | | 1 | |

MEDICINE DISPENSING APPARATUS

TECHNICAL FIELD

The present disclosure relates to a medicine dispensing apparatus.

BACKGROUND ART

WO2016/047487 (PTL 1) discloses that conveyance of a medicine-contained cassette containing medicine sheets, from a cassette shelf to a delivery site, is repeated successively and thereafter conveyance of a medicine-contained cassette from which medicine sheets have been dispensed, from the delivery site back to the cassette shelf, is repeated successively.

CITATION LIST

Patent Literature

PTL 1: WO2016/047487

SUMMARY OF INVENTION

Technical Problem

It is desired for a medicine dispensing apparatus to shorten the time required for dispensing medicines. While the above-referenced document discloses that the time required for dispensing medicine sheets is shortened by operations such as an operation of increasing the moving speed of the medicine-contained cassette, and an operation of moving the medicine-contained cassette in parallel with dispensing medicine sheets from the medicine-contained cassette, there still remains a room for improvement.

The present disclosure proposes a medicine dispensing apparatus capable of further shortening the time required for dispensing medicines.

Solution to Problem

According to the present disclosure, a medicine dispensing apparatus is proposed including a conveyer that conveys a medicine container, and a conveyance control unit that controls conveyance of the medicine container by the conveyer. The conveyer conveys a medicine container, from a storage site storing a plurality of the medicine containers each containing a medicine, to a delivery site where the medicine contained in the medicine container is removed from the medicine container. The conveyer returns, from the delivery site to the storage site, the medicine container from which the contained medicine is partially removed. A standby site where the medicine container unloaded from the storage site and directed toward the delivery site is allowed to stand by is located between the storage site and the delivery site. The medicine dispensing apparatus further includes a determination unit that determines whether or not the medicine contained in the medicine container conveyed to the delivery site for medicine preparation is to be used also for subsequent medicine preparation. The conveyance control unit returns the medicine container containing the medicine determined, by the determination unit, not to be used for the subsequent medicine preparation, from the standby site to the storage site. The conveyance control unit causes the medicine container containing the medicine determined, by the determination unit, to be used also for the subsequent medicine preparation, to stand by at the standby site until the subsequent medicine preparation, without being returned to the storage site.

In the medicine dispensing apparatus, the conveyance control unit may cause the medicine container containing the medicine to be used for the subsequent medicine preparation, to be conveyed, during medicine preparation, from the storage site to the standby site.

In the medicine dispensing apparatus, the conveyance control unit may cause the medicine container from which the medicine is removed at the delivery site, to be conveyed to the storage site through the standby site.

In the medicine dispensing apparatus, between the storage site and the delivery site, a second standby site where the medicine container to be returned from the delivery site to the storage site is allowed to stand by may be located, and the conveyance control unit may cause the medicine container from which the medicine is removed at the delivery site, to be conveyed to the storage site through the second standby site.

In the medicine dispensing apparatus, the storage site may have an unloading-loading port for the medicine container, the medicine dispensing apparatus may further include a placement determination unit that determines placement of the medicine container at the storage site, and the placement determination unit may place the medicine container containing the medicine conveyed at a higher frequency to the delivery site based on a past history, so that the medicine container is closer to the unloading-loading port at the storage site.

The medicine dispensing apparatus may further include an informing unit that informs, a user who uses the medicine dispensing apparatus, of the placement of the medicine container at the storage site.

The medicine dispensing apparatus may further include a position change unit that changes a position of the medicine container at the storage site.

In the medicine dispensing apparatus, when the medicine container is returned to the storage site, the placement of the medicine container at the storage site may be changed.

In the medicine dispensing apparatus, while the medicine container is not unloaded from the storage site, the placement of the medicine container at the storage site may be changed.

In the medicine dispensing apparatus, a user who uses the medicine dispensing apparatus may remove the medicine from the medicine container at the delivery site.

The medicine dispensing apparatus may further include a medicine removal unit that removes the medicine from the medicine container at the delivery site.

In the medicine dispensing apparatus, the medicine container may be a box or a cassette.

Advantageous Effects of Invention

With the medicine dispensing apparatus according to the present disclosure, the time required for dispensing medicines can further be shortened.

BRIEF DESCRIPTION OF DRAWINGS

FIG. 8 is a schematic diagram showing conveyance of a medicine container containing a medicine(s) to be used also for the subsequent medicine preparation.

FIG. 9 is a schematic diagram showing conveyance, during medicine preparation, of a medicine container containing a medicine(s) to be used for the subsequent medicine preparation.

FIG. 10 is a table showing an example of a medicine preparation history.

DESCRIPTION OF EMBODIMENTS

Figure 1:
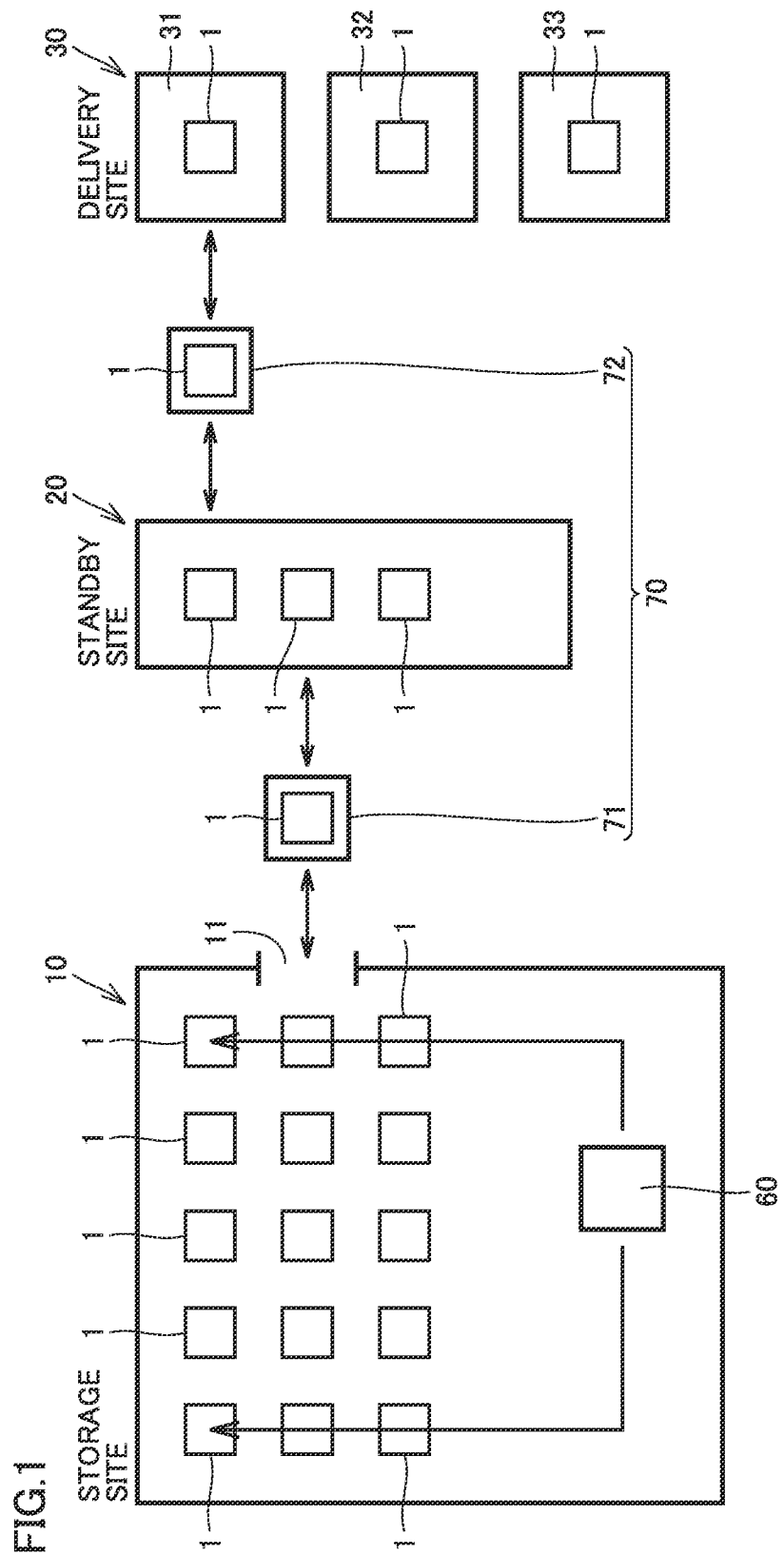
FIG. 1 is a schematic diagram showing a general configuration of a medicine dispensing apparatus.

Embodiments are described hereinafter based on the drawings. In the following description, the same parts are denoted by the same reference characters. They are named identically and function identically. A detailed description thereof is therefore not repeated.

Overall Configuration of Medicine Dispensing Apparatus

FIG. 1 is a schematic diagram showing a general configuration of a medicine dispensing apparatus. The medicine dispensing apparatus dispenses a medicine(s) based on a prescription. The prescription is issued by a doctor to a patient. The prescription indicates prescription information. The prescription information includes medicine information. The medicine information includes medicine name, dose, directions for use, and dosage. As shown in FIG. 1, the medicine dispensing apparatus includes a storage site 10, a standby site 20, a delivery site 30, and a conveyer 70.

Storage site 10 stores a plurality of medicine containers 1. A plurality of medicine containers 1 each contain a medicine(s). Medicine container 1 supplies a solid medicine as a medicine, for example. Examples of the solid medicine are tablet, pill, capsule, and the like. Medicine container 1 is a box containing medicines of the same type, for example. A PTP (Press Through Package) sheet in which a plurality of medicines are packaged in PTP may be contained in the box. Medicine container 1 is, for example, a medicine cassette capable of containing a plurality of medicines of the same type and dispensing contained medicines one by one.

At delivery site 30, medicines contained in medicine container 1 are removed from medicine container 1. At delivery site 30, a user who uses the medicine dispensing apparatus may remove medicines from medicine container 1. Alternatively, the medicine dispensing apparatus may further includes a medicine removal unit that is a device for removing medicines from medicine container 1 at delivery site 30.

Delivery site 30 shown in FIG. 1 includes a first delivery unit 31, a second delivery unit 32, and a third delivery unit 33. In each of a plurality of delivery units, medicines can be removed from medicine container 1. The medicine dispensing apparatus have a plurality of delivery units to thereby enable parallel removal of medicines from medicine containers 1 in the plurality of delivery units based on respective different pieces of prescription information. Delivery site 30 may not necessarily be provided with a plurality of delivery units, and delivery site 30 may have only one delivery unit.

Standby site 20 is located between storage site 10 and delivery site 30. Standby site 20 allows medicine container 1 unloaded from storage site 10 and directed toward delivery site 30 to stand by. Medicine container 1 is conveyed from storage site 10 through standby site 20 to delivery site 30. Medicine container 1 is conveyed from standby site 20 to any of first delivery unit 31, second delivery unit 32, or third delivery unit 33. Medicine container 1 from which medicines have been removed at delivery site 30 is returned through the same standby site 20 to storage site 10. Standby site 20 can allow a plurality of medicine containers 1 to stand by.

Conveyer 70 transports medicine container 1 between storage site 10 and delivery site 30. Conveyer 70 transports medicine container 1 from storage site 10 to delivery site 30. Conveyer 70 returns medicine container 1 from which the contained medicine has been removed partially, from delivery site 30 to storage site 10. Conveyer 70 includes a first conveyer unit 71 and a second conveyer unit 72. First conveyer unit 71 transports medicine container 1 between storage site 10 and standby site 20. Second conveyer unit 72 transports medicine container 1 between standby site 20 and delivery site 30. The double-headed arrows shown leftward and rightward of each of first conveyer unit 71 and second conveyer unit 72 indicate the directions in which first conveyer unit 71 and second conveyer unit 72 can move, and accordingly indicate the directions in which medicine container 1 can be conveyed.

Storage site 10 has an unloading-loading port 11 for medicine container 1. Medicine container 1 directed from storage site 10 toward delivery site 30 is unloaded from storage site 10 through unloading-loading port 11. Medicine container 1 to be returned from delivery site 30 to storage site 10 is loaded through unloading-loading port 11 into storage site 10.

The medicine dispensing apparatus further includes a position change unit 60. Position change unit 60 is located at storage site 10. Position change unit 60 is freely movable relative to storage site 10 as indicated by the arrows in FIG. 1. Position change unit 60 is capable of changing the position of medicine container 1 at storage site 10. Position change unit 60 is, for example, a robot arm capable of gripping and moving medicine container 1.

Electrical Configuration of Medicine Dispensing Apparatus

Figure 2:
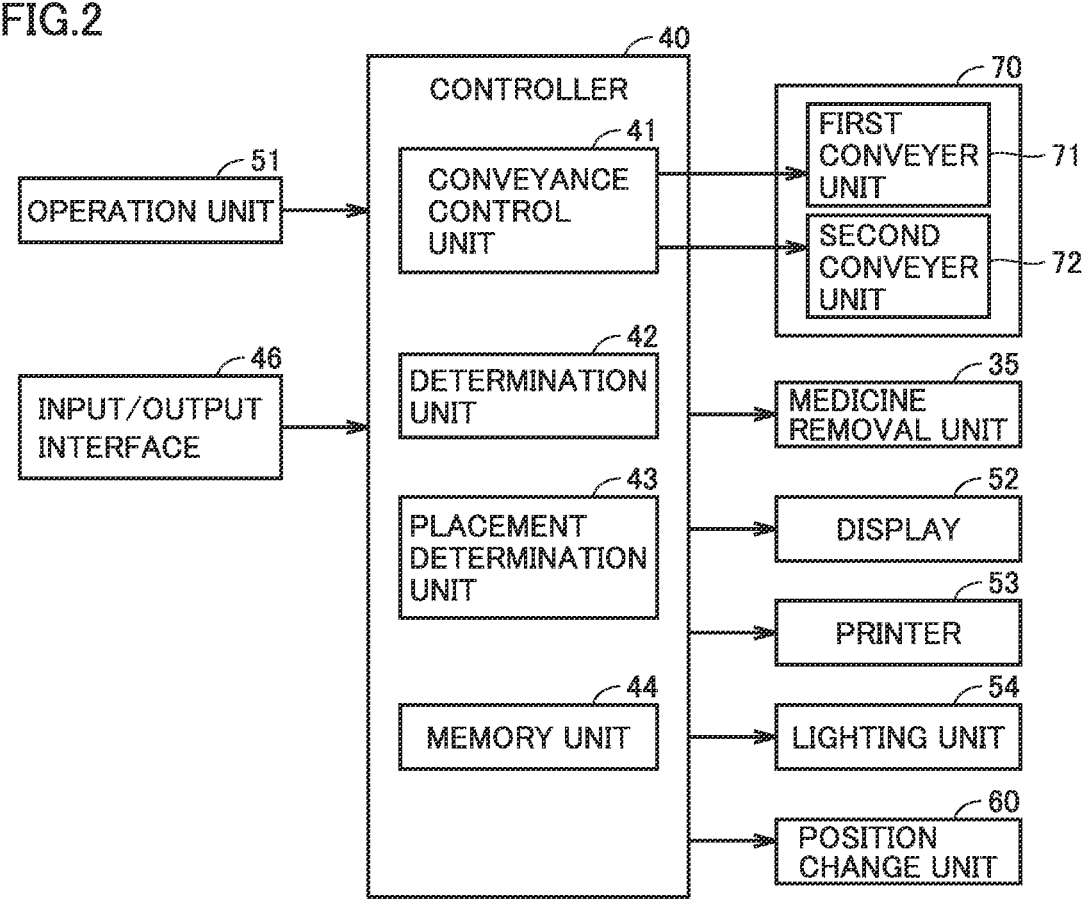
FIG. 2 is a block diagram showing an electrical configuration of the medicine dispensing apparatus.

FIG. 2 is a block diagram showing an electrical configuration of the medicine dispensing apparatus. It should be noted that the block diagram shown in FIG. 2 illustrates only functional blocks of a partial configuration relating to movement of medicine container 1, in the configuration of the medicine dispensing apparatus, and does not necessarily illustrate all functional blocks of the whole configuration of the medicine dispensing apparatus.

The medicine dispensing apparatus includes a controller 40. Controller 40 performs various kinds of arithmetic processing and control. Controller 40 includes a memory unit 44. Memory unit 44 is provided as a region storing a program for performing various kinds of medicine dispensing operations, and storing necessary information. Based on the program and the information stored in memory unit 44, controller 40 controls the overall operation of the medicine dispensing apparatus.

A conveyance control unit 41 controls conveyance of medicine container 1 by conveyer 70. Conveyance control unit 41 transmits a control signal to first conveyer unit 71. Conveyance control unit 41 causes specific medicine container 1 among a plurality of medicine containers 1 stored at storage site 10, to be conveyed from storage site 10 to a specific position at standby site 20. Conveyance control unit 41 causes medicine container 1 that stands by at a specific position at standby site 20, to be conveyed from standby site 20 to storage site 10.

Conveyance control unit 41 transmits a control signal to second conveyer unit 72. Conveyance control unit 41 causes medicine container 1 that stands by at a specific position at standby site 20, to be conveyed to specific delivery site 30. Conveyance control unit 41 causes medicine container 1 to be conveyed from standby site 20 to any of first delivery unit 31, second delivery unit 32, or third delivery unit 33. Conveyance control unit 41 causes medicine container 1 to be conveyed from specific delivery site 30 to a specific position at standby site 20.

A determination unit 42 determines whether or not a medicine contained in medicine container 1 conveyed to delivery site 30 for medicine preparation is to be used also for the subsequent medicine preparation. Conveyance control unit 41 controls conveyance of medicine container 1 by conveyer 70, in accordance with the result of the determination by determination unit 42.

A placement determination unit 43 determines placement of each of a plurality of medicine containers 1 at storage site 10. Controller 40 performs control for changing placement of each medicine container 1 in accordance with the placement determined by placement determination unit 43.

An operation unit 51 is operated by a user who uses the medicine dispensing apparatus. The user operates operation unit 51 to thereby cause information necessary for operation of the medicine dispensing apparatus, to be input to controller 40. The information input to controller 40 is prescription data based on a prescription, for example.

An input/output interface 46 is, for example, an interface for connection to an external device, and typically a USB (Universal Serial Bus) port or the like. Alternatively, input/output interface 46 is, for example, an interface for communication via a communication network, and typically a wired LAN (Local Area Network) module or wireless LAN module, or the like. The prescription data may be input to controller 40 from the external device through input/output interface 46.

A medicine removal unit 35 is provided at delivery site 30. Medicine removal unit 35 is a device for removing a medicine(s) from medicine container 1 at delivery site 30. Medicine removal unit 35 receives a control signal transmitted from controller 40 to remove a predetermined number/quantity of medicine(s) from medicine container 1 containing prescribed medicine(s).

A display 52 is a display unit capable of displaying information. From controller 40 to display 52, information to be indicated on display 52 is output. The information indicated on display 52 includes placement of medicine container 1 at storage site 10. A user who uses the medicine dispensing apparatus can see display 52 to recognize where each medicine container 1 is placed. When operation unit 51 is implemented by a touch panel, operation unit 51 may further serve as display 52.

A printer 53 prints information. Information to be output from printer 53 is output from controller 40 to printer 53. The information to be printed by printer 53 includes placement of medicine container 1 at storage site 10. A user who uses the medicine dispensing apparatus can see the printed matter generated through printing by printer 53 to recognize the position where each medicine container 1 is to be placed.

A lighting unit 54 is implemented for example by an LED (Light Emitting Diode). The medicine dispensing apparatus includes a plurality of lighting units 54. Typically, the medicine dispensing apparatus includes the same number of lighting units 54 as the number of positions where medicine containers 1 can be placed at storage site 10, and each lighting unit 54 is attached at a respective position where medicine container 1 can be placed. From controller 40 to lighting units 54, a control signal is output that indicates which lighting unit 54 among a plurality of lighting units 54 is to be illuminated. A user who uses the medicine dispensing apparatus can see the illuminated lighting unit 54 to recognize where each medicine container 1 is placed.

Display 52, printer 53, and lighting unit 54 correspond to an informing unit according to embodiments that informs, a user who uses the medicine dispensing apparatus, of placement of medicine container 1 at storage site 10. The informing unit informs the user of the placement of medicine container 1. When the user changes the position of medicine container 1 at storage site 10, the user can see display 52 or printed matter produced by printer 53 and check it against this medicine container 1, or identify illuminated lighting unit 54, to recognize the position where medicine container 1 is to be placed at storage site 10.

Position change unit 60 changes the position of medicine container 1 at storage site 10, in accordance with the placement of medicine container 1 determined by controller 40. The placement of each medicine container 1 is output from controller 40 to position change unit 60. Further, from controller 40 to position change unit 60, a control signal is output that changes the position of each medicine container 1 to a position specified by the determined placement. Position change unit 60 can be configured to change the position of medicine container 1 at storage site 10, to save user's time and effort, and reliably place each medicine container 1 at an appropriate position in storage site 10.

When medicine container 1 is returned to storage site 10, the placement of medicine container 1 at storage site 10 may be changed. At the opportunity of moving medicine container 1 within storage site 10, the position of medicine container 1 is changed, so that medicine container 1 is never moved solely for the purpose of changing the position of medicine container 1, and accordingly, the position of medicine container 1 can be changed efficiently. Alternatively, the placement of medicine container 1 may be changed during a period such as nighttime in which no prescription data is input to controller 40 and therefore no medicine container 1 is unloaded from storage site 10, for example. Thus, the position change of medicine container 1 does not influence medicine dispensing, and the placement of medicine container 1 can be changed appropriately.

Example of Specific Configuration of Medicine Container 1

Figure 3:
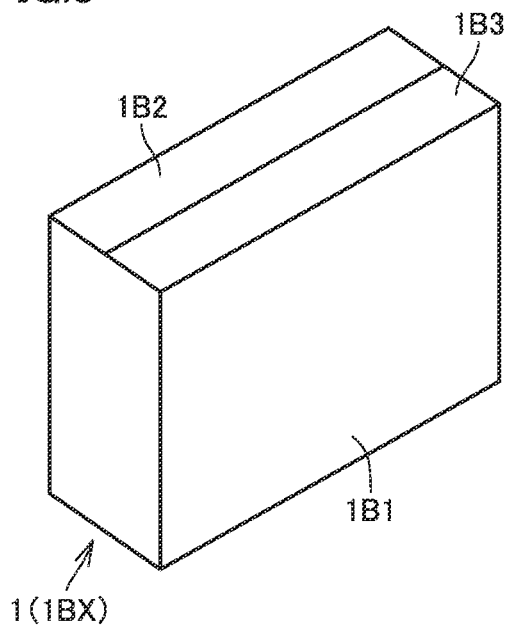
FIG. 3 is a perspective view of a box as an example of a medicine container.

FIG. 3 is a perspective view of a box 1BX that is an example of medicine container 1. Box 1BX shown in FIG. 3 has a box main body 1B1. Box main body 1B1 has an opening and this opening is closed by lids 1B2, 1B3. The opening of box main body 1B1 is typically opened upward.

Figure 4:
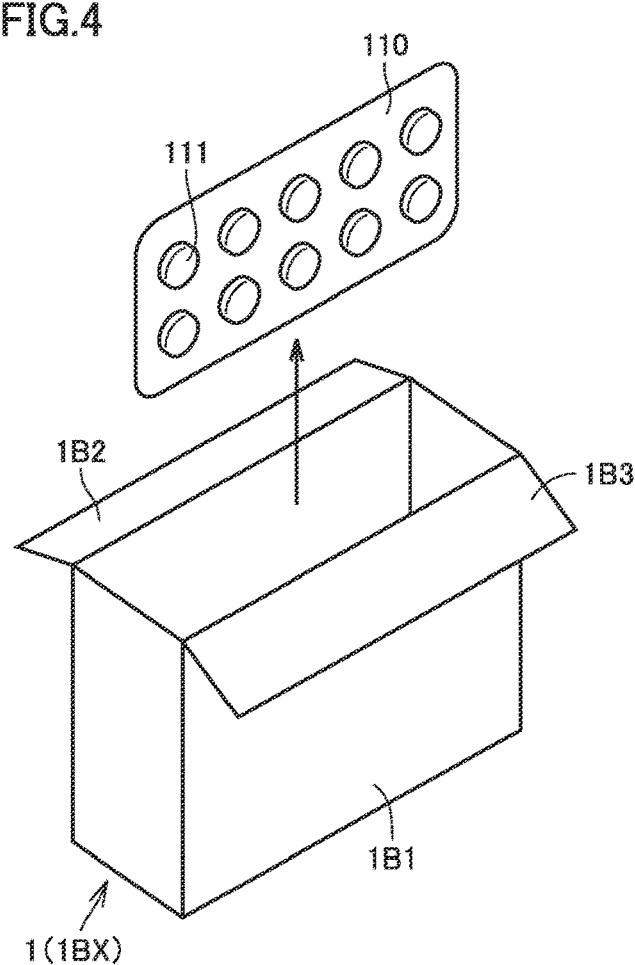
FIG. 4 is a perspective view showing a manner in which medicines are removed from the box showing in FIG. 3.

FIG. 4 is a perspective view showing a manner of removing medicines 111 from box 1BX shown in FIG. 3. Lids 1B2, 1B3 are opened to allow medicines 111 to be removed from box 1BX through the opening of box main body 1B1.

As shown in FIG. 4, a PTP sheet 110 in which a plurality of medicines 111 are packaged in PTP is contained in medicine container 1 (box 1BX). A user who uses the medicine dispensing apparatus removes, from medicine container 1, medicines 111 together with PTP sheet 110. A plurality of PTP sheets 110 are contained in medicine container 1. The user removes, from medicine container 1, a necessary number/quantity of PTP sheet(s) 110 in accordance with prescription data, from a plurality of PTP sheets 110 contained in medicine container 1.

For box 1BX from which a predetermined number of PTP sheets 110 have been removed, the user may close its lids 1B2, 1B3 and temporarily fix lids 1B2, 1B3 with a tape, for example. In this way, box 1BX can be shaped as appropriate to be conveyed.

Figure 5:
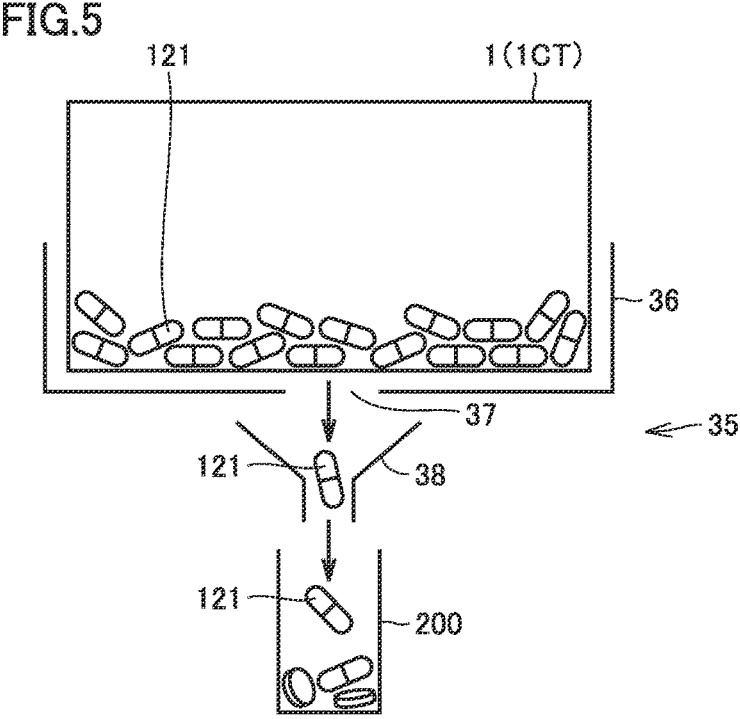
FIG. 5 is a schematic diagram showing a manner in which medicines are removed from a cassette as an example of the medicine container.

FIG. 5 is a schematic diagram showing a manner of removing medicines 121 from a cassette 1CT as an example of medicine container 1. FIG. 5 schematically illustrates an example of medicine removal unit 35 which is also shown in FIG. 2. Cassette 1CT contains a plurality of solid medicines 121. Cassette 1CT shown in FIG. 5 contains a plurality of capsulated medicines.

Cassette 1CT conveyed to delivery site 30 is held in a cassette holder 36. Cassette 1CT is provided with a dispenser (details are not shown) for removing medicines 121 one by one from cassette 1CT. The dispenser and the mechanism of cassette holder 36 cooperate with each other to remove medicines 121 from cassette 1CT. In cassette holder 36, a discharge outlet 37 is formed. Medicine 121 dispensed from cassette 1CT drops through discharge outlet 37 to be received by a hopper 38. Medicine 121 further drops through hopper 38 to be received in a receptacle 200. Receptacle 200 is handed together with the medicines contained therein to a patient. A plurality of different types of medicines may be contained in receptacle 200.

As shown in FIGS. 4 and 5, regardless of whether medicine container 1 is in the shape of box 1BX or the shape of cassette 1CT, and regardless of whether medicines are removed from medicine container 1 by the user or by medicine removal unit 35, a predetermined number/quantity of medicine(s) can be removed accurately from medicine container 1. For medicine container 1 in the form of box 1BX, medicines may be removed from this medicine container 1 by medicine removal unit 35. From medicine container 1 in the form of cassette 1CT, medicines may be removed by the user.

Conveyance Control for Medicine Container 1

Figure 6:
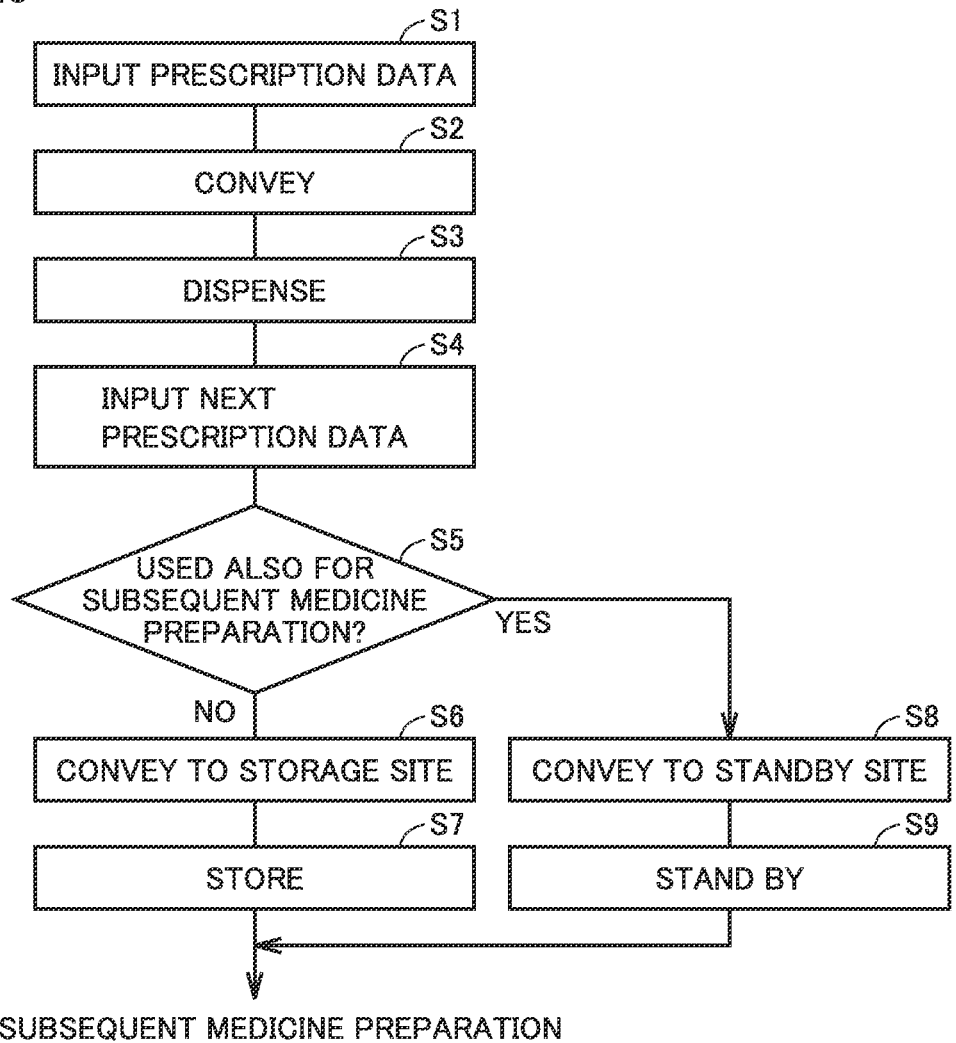
FIG. 6 is a flowchart showing an example of a process of conveying a medicine container.

FIG. 6 is a flowchart showing an example of a process of conveying medicine container 1. Referring to FIG. 6, an example of conveyance control for medicine container 1 is described.

First in step S1, prescription data is input to the medicine dispensing apparatus. A user who uses the medicine dispensing apparatus operates operation unit 51 to input the prescription data to controller 40. Alternatively, the prescription data is input from an external device to controller 40 through input/output interface 46.

Next in step S2, medicine container 1 is conveyed. Controller 40, more specifically conveyance control unit 41, outputs, to first conveyer unit 71, a control signal that causes medicine container 1 containing a medicine included in the input prescription data, to be conveyed from storage site 10 to standby site 20. Receiving the input control signal, first conveyer unit 71 conveys this medicine container 1 from storage site 10 to a specific position in standby site 20. Conveyance control unit 41 further outputs a control signal to second conveyer unit 72. Receiving the input control signal, second conveyer unit 72 conveys medicine container 1 conveyed to standby site 20, from standby site 20 to delivery site 30, specifically to any of first delivery unit 31, second delivery unit 32, or third delivery unit 33. In this way, medicine container 1 is conveyed from storage site 10 to delivery site 30.

Subsequently in step S3, a medicine(s) is dispensed from medicine container 1. As described above with reference to FIGS. 3 and 4, the user opens lids 1B2, 1B3 of box 1BX conveyed to delivery site 30 to remove, from box 1BX, a required number/quantity of PTP sheet(s) 110 in accordance with the prescription data. Alternatively, as described above in connection with FIG. 5, medicine removal unit 35 dispenses a required number/quantity of medicine(s) 121 from cassette 1CT conveyed to delivery site 30. In this way, medicines are dispensed.

In step S4, prescription data for the subsequent medicine preparation is input to the medicine dispensing apparatus. Like step S1, operation unit 51 or input/output interface 46 is used to input, to controller 40, the prescription data for the subsequent medicine preparation. The input of the next prescription data in step S4 may not necessarily be done after dispensing of the medicine(s) in step S3. After the prescription data is input in step S1, the next prescription data may be input during conveyance of medicine container 1 in step S2, during medicine dispensation from medicine container 1 in step S3, or between these steps.

After the input of the next prescription data, it is determined, in step S5, whether or not a medicine(s) included in the prescription data for the ongoing medicine preparation is also included in prescription data for the subsequent medicine preparation. Specifically, it is determined whether or not the medicine(s) contained in medicine container 1 conveyed to delivery site 30 for the ongoing medicine preparation is to be used also for the subsequent medicine preparation. The determination in step S5 is performed by determination unit 42 of controller 40.

When it is determined in step S5 that the medicine(s) used for the ongoing medicine preparation is not to be used for the subsequent medicine preparation (NO in step S5), medicine container 1 is conveyed from delivery site 30 to storage site 10 in step S6.

Figure 7:
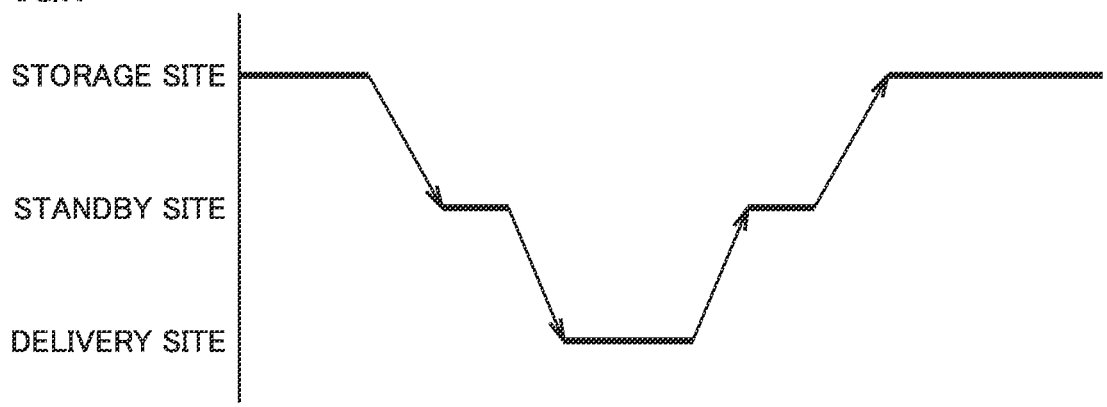
FIG. 7 is a schematic diagram showing conveyance of a medicine container containing a medicine(s) not to be used for the subsequent medicine preparation.

FIG. 7 is a schematic diagram showing conveyance of medicine container 1 containing a medicine(s) not to be used for the subsequent medicine preparation. As shown in FIG. 7, medicine container 1 which has been conveyed from storage site 10 to delivery site 30 through standby site 20 and from which a medicine(s) has been removed at delivery site 30 is conveyed to storage site 10 through the same standby site 20, when a medicine(s) contained in this medicine container 1 is not to be used for the subsequent medicine preparation. Through the reverse procedure to the conveyance in step S2, second conveyer unit 72 conveys medicine container 1 from delivery site 30 to standby site 20 and first conveyer unit 71 conveys medicine container 1 from standby site 20 to storage site 10.

Medicine container 1 returned to storage site 10 in step S7 is stored at an appropriate position at storage site 10.

When it is determined in step S5 that the medicine(s) used for the ongoing medicine preparation is to be used also for the subsequent medicine preparation (YES in step S5), medicine container 1 is conveyed from delivery site 30 to standby site 20 in step S8.

FIG. 8 is a schematic diagram showing conveyance of medicine container 1 containing a medicine(s) to be used also for the subsequent medicine preparation. As shown in FIG. 8, medicine container 1 which has been conveyed from storage site 10 to delivery site 30 through standby site 20 and from which a medicine(s) has been removed at delivery site 30 is conveyed to standby site 20 without being returned to storage site 10, when a medicine(s) contained in this medicine container 1 is to be used also for the subsequent medicine preparation. Second conveyer unit 72 conveys medicine container 1 from delivery site 30 to standby site 20.

In step S9, medicine container 1 conveyed to standby site 20 stands by at standby site 20 until the subsequent medicine preparation.

After the operation in step S7 or the operation in step S9, the subsequent medicine preparation is started. Referring again to FIG. 8, medicine container 1 caused to stand by at standby site 20 by the operation in step S9 is conveyed from standby site 20 to delivery site 30. At delivery site 30, the medicine(s) is dispensed from medicine container 1. When it is determined that the medicine is not to be used for the subsequent medicine preparation through determination similar to the one in step S5, medicine container 1 is returned to storage site 10 through standby site 20.

In this way, medicine container 1 containing the medicine (s) to be used also for the subsequent medicine preparation is caused to stand by at standby site 20 between delivery site 30 and storage site 10 until the subsequent medicine preparation, rather than being returned from delivery site 30 to storage site 10, and accordingly, medicine container 1 can be conveyed for the subsequent medicine preparation immediately to delivery site 30 to start medicine dispensation. Thus, particularly when medicine preparation is done successively, the time required for the overall medicine dispensation can further be shortened.

FIG. 9 is a schematic diagram showing conveyance, during medicine preparation, of medicine container 1 containing a medicine(s) to be used for the subsequent medicine preparation. FIG. 9 shows conveyance of each of medicine container 1 containing medicine X and medicine container 1 containing medicine Y. Medicine X is first conveyed from storage site 10 to delivery site 30 through standby site 20, and medicine Y is subsequently conveyed from storage site 10 to delivery site 30 through standby site 20. Next prescription data that is input to controller 40 subsequently to prescription data including medicine X may include medicine Y. Medicine X and medicine Y may be included in the same prescription data.

As shown in FIG. 9, during medicine preparation in which medicine container 1 containing medicine X is conveyed to delivery site 30 and medicine X is removed from medicine container 1, medicine container 1 containing medicine Y is conveyed from storage site 10 to standby site 20. In a period in which medicine container 1 containing medicine X is still located at delivery site 30, medicine container 1 containing medicine Y has reached standby site 20. Until the removal of medicine X is completed, medicine Y is caused to stand by at standby site 20.

In this way, during medicine preparation of medicine X, medicine container 1 containing medicine Y to be used for the subsequent medicine preparation is conveyed from storage site 10 to standby site 20 and caused to stand by at standby site 20 so as to make subsequent medicine Y available in advance, to thereby enable shortening of the time interval from completion of removal of medicine X to start of subsequent removal of medicine Y. Accordingly, the time required for medicine dispensation can further be shortened.

While FIG. 9 illustrates that conveyance, by first conveyer unit 71, of medicine container 1 containing medicine Y is started after medicine container 1 containing medicine X reaches delivery site 30, the conveyance is not limited to the illustrated example. Immediately after conveying medicine container 1 containing medicine X from storage site 10 to standby site 20, first conveyer unit 71 may start conveying medicine container 1 containing medicine Y. Conveyance, by first conveyer unit 71, of medicine container 1 containing medicine Y may be started during standby at standby site 20 or during conveyance from standby site 20 to delivery site 30, of medicine container 1 containing medicine X.

After completion of removal of medicine X, second conveyer unit 72 conveys medicine container 1 containing medicine X from delivery site 30 to standby site 20. Second conveyer unit 72 thereafter conveys medicine container 1 containing medicine Y from standby site 20 to delivery site 30. While FIG. 9 illustrates that conveyance, by second conveyer unit 72, of medicine container 1 containing medicine Y is started during conveyance, by first conveyer unit 71, of medicine container 1 containing medicine X, the conveyance is not limited to the illustrated example. In a period in which medicine container 1 containing medicine X is located at standby site 20 or after medicine container 1 containing medicine X is returned to storage site 10, second conveyer unit 72 may start conveying medicine container 1 containing medicine Y from standby site 20 to delivery site 30.

Determination of Placement of Medicine Container 1 at Storage Site 10

FIG. 10 is a table showing an example of a medicine preparation history. The medicine preparation history shown in FIG. 10 is stored in memory unit 44. FIG. 10 shows a past history of medicine dispensation. The medicine preparation history shown in FIG. 10 may be a history of dispensation performed by the medicine dispensing apparatus based on prescription data input to controller 40 in the past. Alternatively, histories of dispensation performed by other medicine dispensing apparatuses may be input together to controller 40 and stored in memory unit 44. When prescription data is newly input to controller 40, the medicine preparation history is updated.

Medicines A to E shown in FIG. 10 represent medicines of respective kinds different from each other. Medicines A to E are contained in respective medicine containers 1 different from each other. FIG. 10 shows a history of which of medicines A to E was dispensed at each of the first to tenth dispensation opportunities.

Specifically, at the first dispensation opportunity, one tablet of medicine A and one tablet of medicine B were dispensed. At the second dispensation opportunity, one tablet of medicine A, one tablet of medicine C, and one tablet of medicine D were dispensed. At the third dispensation opportunity, one tablet of medicine B and one tablet of medicine E were dispensed. At the fourth dispensation opportunity, one tablet of medicine A, one tablet of medicine B, and one tablet of medicine C were dispensed. At the fifth dispensation opportunity, one tablet of medicine A, one tablet of medicine B, and one tablet of medicine D were dispensed.

At the sixth dispensation opportunity, one tablet of medicine A and one tablet of medicine D were dispensed. At the seventh dispensation opportunity, one tablet of medicine A and one tablet of medicine C were dispensed. At the eighth dispensation opportunity, one tablet of medicine A and one tablet of medicine B were dispensed. At the ninth dispensation opportunity, one tablet of medicine C and one tablet of medicine E were dispensed. At the tenth dispensation opportunity, one tablet of medicine A and one tablet of medicine B were dispensed. At the first, eighth, and tenth dispensation opportunities, the same prescription data was input to medicine dispensing apparatus.

From the first to tenth dispensation opportunities, eight tablets of medicine A were dispensed in total, six tablets of medicine B were dispensed in total, four tablets of medicine C were dispensed in total, three tablets of medicine D were dispensed in total, and two tablets of medicine E were dispensed in total. Thus, medicine A was dispensed at the highest frequency, medicine B, medicine C, and medicine D were dispensed at respective frequencies decreasing successively, and medicine E was dispensed at the lowest frequency. Based on the past history of medicine dispensation by the medicine dispensing apparatus, placement determination unit 43 shown in FIG. 2 determines placement of medicine containers 1 at storage site 10 that contain respective medicines. Placement determination unit 43 determines placement of medicine containers 1 so that the time required for conveyance of medicine A dispensed at a higher frequency is shorter.

Figure 11:
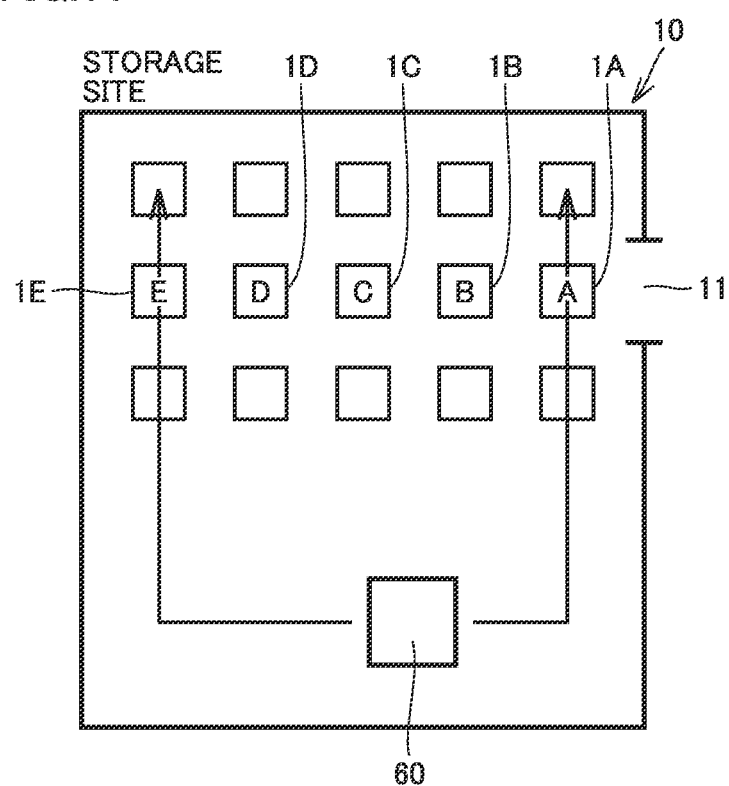
FIG. 11 is a schematic diagram showing placement of medicine containers in a storage site, in accordance with the medicine preparation history shown in FIG. 10.

FIG. 11 is a schematic diagram showing placement of medicine containers 1 at storage site 10, in accordance with the medicine preparation history shown in FIG. 10. A medicine container 1A shown in FIG. 11 is a medicine container containing medicine A. A medicine container 1B is a medicine container containing medicine B. A medicine container 1C is a medicine container containing medicine C. A medicine container 1D is a medicine container containing medicine D. A medicine container 1E is a medicine container containing medicine E.

Medicine container 1 containing a medicine dispensed at a higher frequency in the past history, i.e., conveyed a larger number of times to delivery site 30, is placed, at storage site 10, closer to unloading-loading port 11 for medicine containers 1. As shown in FIG. 11, medicine container 1A is placed closest to unloading-loading port 11, medicine container 1B is placed further from unloading-loading port 11 than medicine container 1A and, similarly, medicine container 1C, medicine container 1D, and medicine container 1E are each placed still further in this order from unloading-loading port 11.

In view of the time required for medicine container 1 to move to unloading-loading port 11 of storage site 10, and thus in view of the time required for medicine container 1 to be conveyed to delivery site 30, the placement of medicine container 1 at storage site 10 is determined. Medicine A dispensed at a higher frequency can be placed closer to unloading-loading port 11, to shorten the time required for dispensing medicine A. Accordingly, the overall time required for the medicine dispensing apparatus to dispense medicines can be shortened and the productivity can be improved.

Medicine Dispensing Apparatus Including Second Standby Site 21

Figure 12:
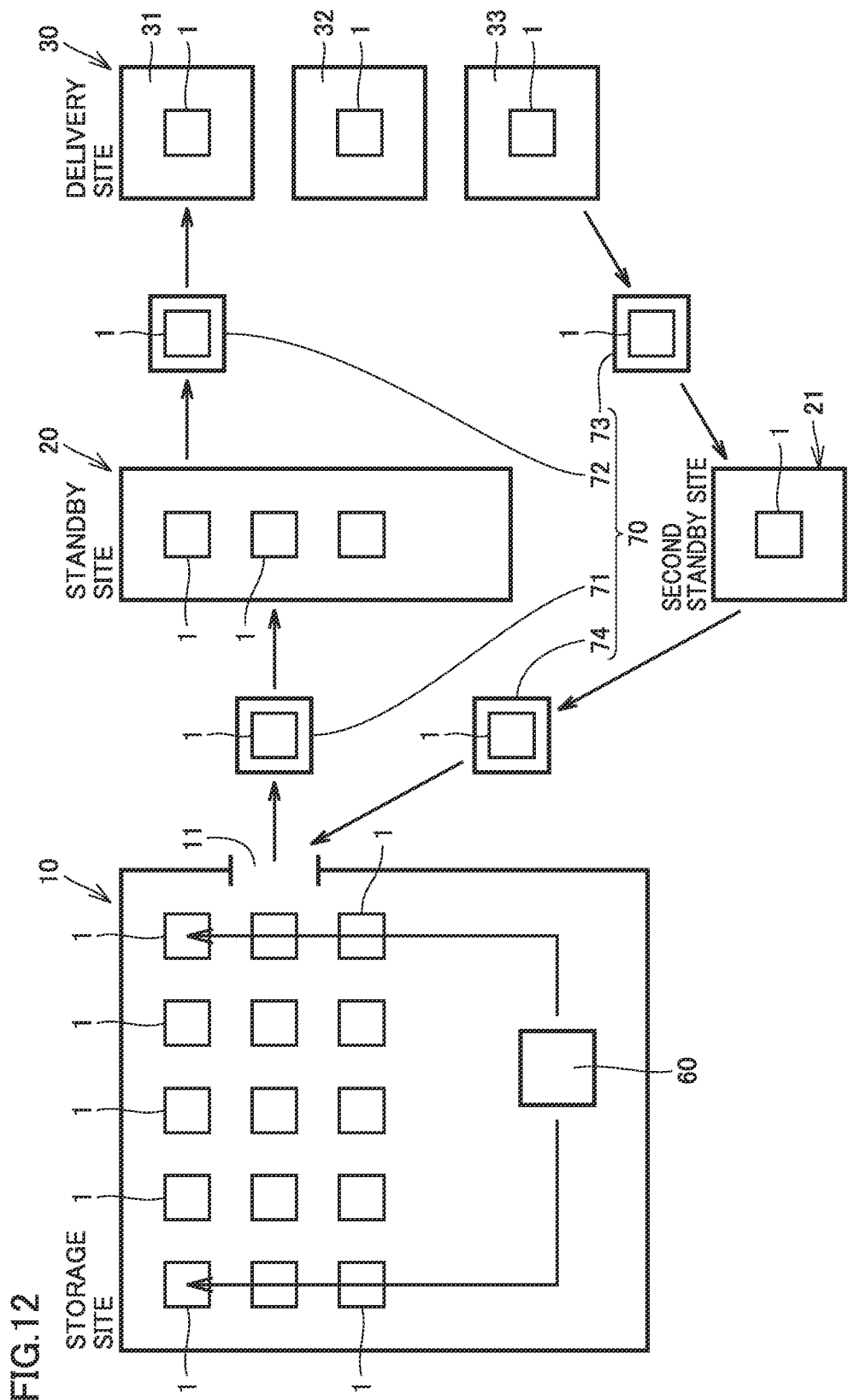
FIG. 12 is a schematic diagram showing a general configuration of a medicine dispensing apparatus including a second standby site.

FIG. 12 is a schematic diagram showing a general configuration of a medicine dispensing apparatus including a second standby site 21. The medicine dispensing apparatus shown in FIG. 12 includes second standby site 21 in addition to the configuration described above with reference to FIG. 1.

Second standby site 21 is located between storage site 10 and delivery site 30. Second standby site 21 allows medicine container 1 to be returned from delivery site 30 to storage site 10, to stand by at second standby site 21. After the medicine is removed from medicine container 1 at any of first delivery unit 31, second delivery unit 32, or third delivery unit 33, medicine container 1 is conveyed to second standby site 21. Medicine container 1 is returned from second standby site 21 to storage site 10. Medicine container 1 from which its medicine is removed at delivery site 30 is conveyed to storage site 10 through second standby site 21.

Conveyer 70 includes a third conveyer unit 73 and a fourth conveyer unit 74. Third conveyer unit 73 conveys medicine container 1 between delivery site 30 and second standby site 21. Fourth conveyer unit 74 conveys medicine container 1 between second standby site 21 and storage site 10.

In FIG. 12, arrows shown around first conveyer unit 71, second conveyer unit 72, third conveyer unit 73, and fourth conveyer unit 74 each indicate the direction in which medicine container 1 is conveyed. First conveyer unit 71, second conveyer unit 72, third conveyer unit 73, and fourth conveyer unit 74 are also movable in the opposite direction to the direction of the arrows. For example, third conveyer unit 73 carrying medicine container 1 can move from delivery site 30 to second standby site 21, and can move, without carrying medicine container 1, from second standby site 21 to delivery site 30. Fourth conveyer unit 74 carrying medicine container 1 can move from second standby site 21 to storage site 10, and can move, without carrying medicine container 1, from storage site 10 to second standby site 21.

The medicine dispensing apparatus includes standby site 20 and second standby site 21, medicine container 1 to be conveyed from storage site 10 to delivery site 30 is conveyed through standby site 20, and medicine container 1 to be conveyed from delivery site 30 to storage site 10 is conveyed through second standby site 21. Thus, it is possible to effectively make use of the space in standby site 20 where medicine container 1 can stand by. More specifically, in a configuration where medicine container 1 is conveyed from delivery site 30 to standby site 20, it is required for standby site 20 to have an empty space for this medicine container 1. Medicine container 1 to be returned from delivery site 30 to storage site 10 is conveyed to second standby site 21, which makes it unnecessary to have an empty space, so that the space in standby site 20 can be made use of more effectively.

In contrast, the configuration shown in FIG. 1 in which the medicine dispensing apparatus does not include second standby site 21 and both medicine container 1 to be conveyed from storage site 10 to delivery site 30 and medicine container 1 to be conveyed from delivery site 30 to storage site 10 are conveyed through standby site 20 is advantageous in that the medicine dispensing apparatus can be downsized as a whole.

While embodiments are described hereinabove, it should be construed that the embodiments disclosed herein are given by way of illustration in all respects, not by way of limitation. It is intended that the scope of the present invention is defined by claims, not by the description above, and encompasses all modifications and variations equivalent in meaning and scope to the claims.

REFERENCE SIGNS LIST 1, 1A, 1B, 1C, 1D, 1E medicine container; 1B1 box main body; 1B2, 1B3 lid; 1BX box; 1CT cassette; 10 storage site; 11 unloading-loading port; 20 standby site; 21 second standby site; 30 delivery site; 31 first delivery unit; 32 second delivery unit; 33 third delivery unit; 35 medicine removal unit; 36 cassette holder; 37 discharge outlet; 38 hopper; 40 controller; 41 conveyance control unit; 42 determination unit; 43 placement determination unit; 44 memory unit; 46 input/output interface; 51 operation unit; 52 display; 53 printer; 54 lighting unit; 60 position change unit; 70 conveyer; 71 first conveyer unit; 72 second conveyer unit; 73 third conveyer unit; 74 fourth conveyer unit; 110 PTP sheet; 111, 121 medicine; 200 receptacle

The invention claimed is:

1. A medicine dispensing apparatus comprising:
    a conveyer that
        conveys a medicine container, from a storage site storing a plurality of the medicine containers each containing a medicine, to a delivery site where the medicine contained in the medicine container is removed from the medicine container, and
        returns, from the delivery site to the storage site, the medicine container from which the contained medicine is partially removed; and
    a conveyance control unit that controls conveyance of the medicine container by the conveyer, wherein
    a standby site where the medicine container unloaded from the storage site and directed toward the delivery site is allowed to stand by is located between the storage site and the delivery site,
    the medicine dispensing apparatus further comprises
    a determination unit that determines whether or not the medicine contained in the medicine container conveyed to the delivery site for medicine preparation is to be used also for subsequent medicine preparation, and
    the conveyance control unit
        returns the medicine container containing the medicine determined, by the determination unit, not to be used for the subsequent medicine preparation, from the standby site to the storage site, and
        causes the medicine container containing the medicine determined, by the determination unit, to be used also for the subsequent medicine preparation, to stand by at the standby site until the subsequent medicine preparation, without being returned to the storage site.

2. The medicine dispensing apparatus according to claim 1, wherein the conveyance control unit causes the medicine container containing the medicine to be used for the subsequent medicine preparation, to be conveyed, during medicine preparation, from the storage site to the standby site.

3. The medicine dispensing apparatus according to claim 1, wherein the conveyance control unit causes the medicine container from which the medicine is removed at the delivery site, to be conveyed to the storage site through the standby site.

4. The medicine dispensing apparatus according to claim 1, wherein
    between the storage site and the delivery site, a second standby site where the medicine container to be returned from the delivery site to the storage site is allowed to stand by is located, and
    the conveyance control unit causes the medicine container from which the medicine is removed at the delivery site, to be conveyed to the storage site through the second standby site.

5. The medicine dispensing apparatus according to claim 1, wherein
    the storage site has an unloading-loading port for the medicine container,
    the medicine dispensing apparatus further comprises a placement determination unit that determines placement of the medicine container at the storage site, and
    the placement determination unit places the medicine container containing the medicine conveyed at a higher frequency to the delivery site based on a past history, so that the medicine container is closer to the unloading-loading port at the storage site.

6. The medicine dispensing apparatus according to claim 5, further comprising an informing unit that informs, a user who uses the medicine dispensing apparatus, of the placement of the medicine container at the storage site.

7. The medicine dispensing apparatus according to claim 5, further comprising a position change unit that changes a position of the medicine container at the storage site.

8. The medicine dispensing apparatus according to claim 7, wherein when the medicine container is returned to the storage site, the placement of the medicine container at the storage site is changed.

9. The medicine dispensing apparatus according to claim 7, wherein while the medicine container is not unloaded from the storage site, the placement of the medicine container at the storage site is changed.

10. The medicine dispensing apparatus according to claim 1, wherein a user who uses the medicine dispensing apparatus removes the medicine from the medicine container at the delivery site.

11. The medicine dispensing apparatus according to claim 1, further comprising a medicine removal unit that removes the medicine from the medicine container at the delivery site.

12. The medicine dispensing apparatus according to claim 1, wherein the medicine container is a box or a cassette.

* * * * *